United States Patent [19]

Wiezer et al.

[11] 4,356,308

[45] Oct. 26, 1982

[54] PROCESS FOR THE PREPARATION OF 2,2,6,6-TETRAMETHYLPIPERIDONE-4

[75] Inventors: Hartmut Wiezer; Günther Nowy; Harald Häberlein, all of Gersthofen, Fed. Rep. of Germany

[73] Assignee: Hoechst Aktiengesellschaft, Fed. Rep. of Germany

[21] Appl. No.: 248,563

[22] Filed: Mar. 27, 1981

[30] Foreign Application Priority Data

Apr. 5, 1980 [DE] Fed. Rep. of Germany ....... 3013403

[51] Int. Cl.³ ............................................ C07D 211/74
[52] U.S. Cl. .................................................. 546/242
[58] Field of Search ........................................ 546/242

[56] References Cited

U.S. PATENT DOCUMENTS 3,959,295  5/1976  Orban et al. ......................... 546/242

Primary Examiner—Richard A. Schwartz
Attorney, Agent, or Firm—Connolly and Hutz

[57] ABSTRACT

In the synthesis of 2,2,6,6-tetramethylpiperidone-4 (triacetone-amine) from acetone and ammonia, a partially halogenated or perhalogenated aliphatic or cyclic hydrocarbon is used as catalyst in an amount of from 0.01 to 5 mol %, relative to acetone.

8 Claims, No Drawings

PROCESS FOR THE PREPARATION OF 2,2,6,6-TETRAMETHYLPIPERIDONE-4

2,2,6,6-Tetramethylpiperidone-4, which is also called triacetone-amine and serves preferably as starting material for the manufacture of Hindered Amine Light Stabilizers is a compound known for more than 100 years. It is formed by condensation of acetone with ammonia under the catalytic influence of Lewis acids or protonic acids or the salt thereof with ammonia or amines (German Auslegeschrift No. 1,685,753; German Offenlegungsschriften Nos. 2,429,935, 2,429,936, 2,429,937, 2,429,745, 2,429,746, 2,807,172, 2,910,761).

It has now been found that for the preparation of 2,2,6,6-tetramethylpiperidone-4 from acetone and ammonia surprisingly substances of a totally different kind, that is, partially halogenated or perhalogenated hydrocarbons, can be used as catalysts with excellent results.

The present invention provides therefore a process for the preparation of 2,2,6,6-tetramethylpiperidone-4 by reaction of acetone with ammonia at elevated temperatures in the presence of catalysts and optionally cocatalysts and/or solvents, wherein the catalysts are partially halogenated or perhalogenated, aliphatic or cyclic hydrocarbons liquid or solid at room temperature and having from 1 to 28 or 5 or 6 carbon atoms, respectively; these carbon atoms, in the case where their number is from 2 to 6, may also be linked with one another by nonpolymerizable double bonds.

It was not at all to be expected that the compounds as proposed would be apt for use as catalyst in this context. First of all, due to the extensive literature on the synthesis of triacetone-amine, where always so-called acidic catalysts are employed despite most diverse operational conditions, there was the prejudice that 2,2,6,6-tetramethylpiperidone-4 could be obtained with satisfactory yields in the presence of these catalysts only. On the other hand, it was not to be expected either that substances proved to be inert under these reaction conditions such as carbon tetrachloride or hexachloroethane would have a catalytic activity (see Ullmann, vol. 9 (1975), pp. 416 and 475). It was thus furnish 2,2,6,6-tetramethylpiperidone-4 with a considerably improved selectivity as compared to the hitherto known operation modes: while a selectivity of a maximum 76% is obtained according to the state of the art (German Offenlegungsschrift No. 2,910,761), the selectivity according to the invention is greater than 90%. The result are important technological advantages: on the one hand, the strain on the environment is thus reduced, and on the other the catalysts employed according to the invention can generally be distilled off from the reaction mixture and reused.

Suitable catalysts are partially halogenated or perhalogenated, aliphatic or cyclic hydrocarbons liquid or solid at room temperature. By halogen, there is to be understood preferably chlorine, and furthermore bromine and iodine; different halogen atoms may be present in one molecule. Suitable are therefore aliphatic hydrocarbons substituted by these halogen atoms and having from 1 to about 28, preferably 1 to 12, and especially 1 or 2, carbon atoms, and those having from 2 to 6 carbon atoms where carbon atoms are linked by nonpolymerizable double bonds. Preferred are perhalogenated, especially perchlorinated compounds. Examples are 1,1,1,5-tetrachloropentane, pentachloroethane, tetrabromoethane, carbon tetrachloride, carbon tetrabromide, chlorinated paraffins, hexachloroethane, trichloroethylene, tetrachloroethane or perchlorobutadiene. Appropriate halogen-containing cyclic hydrocarbons have 5 or 6 carbon atoms; also in this case carbon atoms may be linked by nonpolymerizable double bonds. These may be mentioned, for example, chlorinated cyclohexanes, hexachlorobenzene and hexachlorocyclopentadiene. Particularly suitable are perchlorinated or perbrominated methane and ethanes substituted by 4 to 6 chlorine or bromine atoms; carbon tetrachloride being especially preferred.

The catalysts are used in amounts of from 0.01 to 5, preferably 0.1 to 2, and especially 0.1 to 1 mol %, relative to acetone. Cocatalysts may be added in an amount of from 0.1 to 0.5%, relative to acetone. Suitable are for example inorganic isothiocyanates, iodides, bromides or sulfides.

The molar ratio of acetone to ammonia is preferably from 30:1 to 2.5:1, especially 15:1 to 4:1, the reaction temperature is in a range of from 20° to 120° C., preferably 50° to 100° C., and especially 70° to 90° C.

The starting material acetone can be replaced partially by condensation products of acetone having a lower boiling point than the final product which are formed in the reaction, such as mesityl oxide, diacetone alcohol, diacetone-amine, phorone, acetonine (or even triacetone-amine distilled off in small amounts together with the low-boiling products after complete reaction), and may contain small amounts of water, in the form of a mixture or as individual components, without encountering the risk of an unfavorable course of the reaction. Since thus the distillate of low-boiling substances consisting of the above compounds in addition to acetone can be reused, nearly quantitative yields are obtained. When after repeated use of the low-boiling fraction a too high water content (more than about 5%) has formed therein, this content can be drastically reduced by short-time stirring of the distillate with alkali metal hydroxide, optionally in the form of highly concentrated aqueous solutions such as sodium hydroxide solution, and separation of the organic phase.

The process can be carried out in the presence or absence of organic solvents. As solvents there may be mentioned aliphatic or aromatic hydrocarbons liquid at room temperature, ethers and alcohols. Especially important are mono- and polyfunctional alcohols, preferably, however, methanol or ethanol, because they serve not only as solvent, but also, when used in amounts of from 5 to 30 mol % relative to acetone, act as solubilizer and carrier for the gaseous ammonia.

The 2,2,6,6-tetramethylpiperidone-4 obtained with good yields according to the operation mode of the invention is used as intermediate, as already mentioned, for example in the manufacture of piperidine stabilizers.

The following examples illustrate the invention.

EXAMPLE 1

116 g of gaseous ammonia are introduced at 10°–30° C. into a mixture of 2,500 g (43.1 mol) of acetone, 150 g of methanol and 10 g of freshly distilled carbon tetrachloride (0.06536 mol=0.1516 mol %=0.4 weight %, relative to acetone); the molar ratio of acetone to ammonia being 6.137:1. The solution is given into a 5 liter autoclave with agitator, made from stainless steel, heated for 5 hours at 80° C., and then allowed to cool. According to gas chromatography determination, the reaction solution contained 3.9% of acetonine (=2,2,4,4,6-pentamethyl-1,3,4,5-tetrahydropyrimidine), 18.8% of 2,2,6,6-tetramethylpiperidone-4 and no high-boiling by-products to be rejected (H₂O is removed in the GC column).

The crude solution is stirred with 150 g of NaOH flakes for 30 minutes at room temperature, the aqueous alkaline phase so formed (350 g) is separated and the organic phase is subjected to fractional distillation. 450 g of 2,2,6,6-tetramethylpiperidone-4 (99.1% strength according to GC) are obtained. 90 g of a resinous residue remain.

Taking into consideration the fact that the low-boiling substances are reused, this result corresponds to a selectivity after distillation of 96.5%.

EXAMPLES 2 to 12

Mixtures of 2,500 g of acetone and 150 g of methanol each were reacted for 5 hours according to Example 1 with modification of the ammonia amount, the temperature and the catalysts. Work-up was then as described before. The test results and data are listed in the following Table.

Alternatively, work-up may be as follows: first the components having a lower boiling point than triacetoneamine are distilled off in a water jet vacuum, and then the residue is crystallized at temperatures below 25° C. according to the indications of German Offenlegungsschrift No. 3,008,536 with addition of a nonpolar solvent selected from the group of (cyclo)aliphatic hydrocarbons, tetrachloroethane and carbon-tetrachloride. This method yields an especially pure triacetone-amine.

distilled off the whole batch, no residue remained, which demonstrates that in the process of the invention the carbon tetrachloride as such acts as catalyst, and not a cleavage product or reaction product thereof, since obviously such a product is not formed under the conditions of the process of the invention.

What is claimed is:

1. A process for the preparation of 2,2,6,6-tetramethylpiperidone-4 by reaction of acetone with ammonia at elevated temperatures in the presence of a catalyst, wherein the catalyst is a partially halogenated or perhalogenated, aliphatic or cyclic hydrocarbon which is liquid or solid at room temperature and has from 1 to 28 or 5 or 6 carbon atoms, respectively; these carbon atoms, in the case where their number is from 2 to 6, may also be linked to one another by nonpolymerizable double bonds.

2. The process of claim 1, wherein the catalyst amount is from 0.01 to 5 mol %, relative to acetone, the molar ratio of acetone to ammonia is from 30:1 to 2.5:1 and the operations are carried out at 20° to 120° C.

3. The process of claim 1 or 2, wherein the catalyst is a perchlorinated or perbrominated methane or an ethane substituted by 4 to 6 chlorine or bromine atoms.

4. The process of claim 1, wherein the process is carried out in the presence of 5–30 mol % of an organic solvent, liquid at room temperature, which is selected from an ether, a mono- or polyfunctional alcohol, an aliphatic hydrocarbon, or an aromatic hydrocarbon.

5. The process of claim 1, wherein the active components for the reaction consist essentially of the acetone,

| Ex. No. | NH₃(g) = mol. %[1] | Catalyst (g) = mol. %[1] | Temperature (°C.) | Yields relative to acetone | | | |
|---|---|---|---|---|---|---|---|
| | | | | Triacetone-amine | | High boiling substances | |
| | | | | g | % | g | % |
| 2 | 114 g/6.4 | CCl₄ 10 g/0.15 | 70 | 395 g | 17.7% | 73 g | 3.3% |
| 3 | 155 g/4.73 | CCl₄ 50 g/0.75 | 70 | 317 g | 14.2% | 221 g | 9.9% |
| 4 | 134 g/5.47 | CCl₄ 50 g/0.75 | 80 | 594 g | 26.7% | 293 g | 13.2% |
| 5 | 97 g/7.55 | (CCl₃)₂ 10 g/0.09 | 80 | 498 g | 22.4% | 125 g | 5.6% |
| 6 | 103 g/7.11 | (CHCl₂)₂ 20 g/0.28 | 80 | 524 g | 23.5% | 115 g | 5.2% |
| 7 | 100 g/7.3 | (CHBr₂)₂ 20 g/0.12 | 80 | 501 g | 25.5% | 153 g | 6.9% |
| 8 | 100 g/7.3 | CCl₃.CHCl₂ 20 g/0.23 | 80 | 460 g | 20.7% | 130 g | 5.8% |
| 9 | 90 g/8.1 | CCl₃(CH₂)₃CH₂Cl 20 g/0.22 | 80 | 235 g | 10.6% | 45 g | 2.0% |
| 10 | 100 g/7.3 | CCl₂=Cl—CCl=CCl₂ 20 g/0.17 | 80 | 250 g | 11.2% | 25 g | 1.1% |
| 11 | 105 g/6.79 | hexachloro-cyclopentadien 20 g/0.17 | 80 | 365 g | 16.4% | 300 g | 13.5% |
| 12 | 100 g/7.33 | chlorinated paraffin 70% chlorine 10 g/0.017 | 80 | 474 g = | 21.3% | 120 g | 5.4% |

[1]relative to acetone

EXAMPLE 13

2,500 g of the low-boiling substances distilled off in the Examples 2 to 4 (containing carbon tetrachloride used as catalyst in these batches) were reacted at 80° C. with 100 g of NH₃ as indicated in Example 1.

Yield: 475 g of triacetone-amine and 188 g of high-boiling substances.

EXAMPLE 14

500 g of toluene and 50 g of carbon tetrachloride were maintained for 5 hours at a temperature of 100° C. under an ammonia pressure of 10 bar. After having the ammonia, and said catalyst.

6. The process of claim 5, wherein the reaction medium includes an organic liquid solvent selected from an ether, a mono- or polyfunctional alcohol, an aliphatic hydrocarbon, or an aromatic hydrocarbon.

7. The process of claim 6, wherein the reaction medium includes 0.1 to 0.5 mol %, relative to the acetone, of an inorganic cocatalyst.

8. The process of claim 1 or 3, wherein the acetone is replaced partially by at least one condensation product of acetone having a lower boiling point than the final product obtained in the work up of previous batches.

\* \* \* \* \*